US00PP21272P3

(12) United States Plant Patent

Leis et al.

(10) Patent No.: US PP21,272 P3

(45) Date of Patent: Sep. 7, 2010

(54) APPLE TREE NAMED 'RGLORS'

(50) Latin Name: ***Malus domestica* Borkh**
Varietal Denomination: RGLORS

(75) Inventors: Michelangelo Leis, Ferrara (IT); Gualtiero Mazzoni, Ferrara (IT)

(73) Assignee: Societa Agricola Mazzoni S.S., Tresigallo Fe (IT)

( * ) Notice: Subject to any disclaimer, the term of this patent is extended or adjusted under 35 U.S.C. 154(b) by 13 days.

(21) Appl. No.: 12/322,190

(22) Filed: Jan. 30, 2009

(65) Prior Publication Data

US 2009/0199315 P1 Aug. 6, 2009

(30) Foreign Application Priority Data

Feb. 6, 2008 (QZ) ..... PRB 2008/0297

(51) Int. Cl.
*A01H 5/00* (2006.01)

(52) U.S. Cl. ..... Plt./161

(58) Field of Classification Search ..... Plt./161, Plt./172

See application file for complete search history.

*Primary Examiner*—Kent L Bell
(74) *Attorney, Agent, or Firm*—Foley & Lardner LLP

(57) ABSTRACT

A new and distinct *Malus domestica* Borkh. apple tree variety named 'RGLORS', particularly characterized by solid russet skin color of the fruit; very crispy flesh of the fruit; and sour to sweet flavor with a sweet aftertaste of the fruit.

3 Drawing Sheets

Latin name of the genus and species of the plant claimed: *Malus domestica* Borkh.

Variety denomination: 'RGLORS'.

PRIORITY CLAIM

This application claims priority under 35 U.S.C. § 119(f) of the European Union—Community Plant Variety Rights No. 2008/0297 filed Feb. 6, 2008.

BACKGROUND OF THE INVENTION

The present invention relates to a new and distinct variety of apple tree, botanically known as *Malus domestica* Borkh. of the Rosaceae family, and hereinafter referred to by the variety denomination 'RGLORS'.

The new *Malus* variety 'RGLORS' was discovered by the inventors, Gualtiero Mazzoni and Michelangelo Leis, in October of 2005 in a block of *Malus domestica* Borkh. apple trees designated 'Rosy Glow' (unpatented, described in U.S. Publication No.: 2004/0168235; also U.S. Plant patent application Ser. Nos. 10/160,991, 10/712,783, and 11/166,062 all now abandoned) growing in a cultivated area of an apple farm located in Migliaro, Ferrara, Italy. The new *Malus* variety 'RGLORS' originated as a naturally occurring sport mutation of a limb of one of the 'Rosy Glow' apple trees growing in the apple farm located in Migliaro, Ferrara, Italy. The new *Malus* 'RGLORS' was selected by the inventors based on the distinctly different fruit characteristics of 'RGLORS' (solid russet skin color, very crisp flesh, and sour-sweet flavor with a sweet aftertaste) from the fruit of 'Rosy Glow'.

The new *Malus* 'RGLORS' was first selected for propagation and further testing by the inventors in 2005 in a controlled environment in Migliaro, Ferrara, Italy. Asexual reproduction of the new *Malus* variety 'RGLORS' by grafting and budding onto M9 rootstock (unpatented variety) was first performed in January of 2006 in an apple farm located in Migliaro, Ferrara, Italy, and has demonstrated that the combination of characteristics as herein disclosed for the new variety are firmly fixed and retained through successive generations of asexual reproduction. The new variety reproduces true to type.

BRIEF DESCRIPTION OF THE INVENTION

The following traits have been repeatedly observed and are determined to be unique characteristics of 'RGLORS' which in combination distinguish this apple tree as a new and distinct variety:

1. Solid russet skin color of the fruit;
2. Very crisp flesh of the fruit; and
3. Sour to sweet flavor with a sweet aftertaste of the fruit.

In comparison to the parental variety, *Malus* variety 'Rosy Glow' (unpatented, described in U.S. Publication No.: 2004/0168235; also U.S. Plant patent application Ser. Nos. 10/160,991, 10/712,783, and 11/166,062 all now abandoned), the new *Malus* variety 'RGLORS' is distinguished by the following traits described in Table 1:

TABLE 1

| Characteristic | New Variety 'RGLORS' | Parental & Comparison Variety 'ROSY GLOW' (unpatented) |
|---|---|---|
| Fruit Skin | Solid russet of fruit skin | Bright red-pink solid blush with very slight darker red-pink striping |
| Fruit Flesh | Very crisp | Slightly fibrous |
| Fruit Flavor | Sour to sweet flavor with sweet aftertaste | Sweet to sour flavor with tart aftertaste |

Of the many commercial varieties known to the present inventors, the most similar in comparison to the new *Malus* variety 'RGLORS' is the parental variety 'Rosy Glow' (unpatented, described in U.S. Publication No.: 2004/0168235; also U.S. Plant patent application Ser. Nos. 10/160,991, 10/712,783, and 11/166,062 all now abandoned), and which is compared in Table 1 above.

BRIEF DESCRIPTION OF THE PHOTOGRAPHS

The accompanying photographs illustrate the overall appearance of the new *Malus* variety 'RGLORS' showing the colors as true as is reasonably possible with colored reproductions of this type. Colors in the photographs may differ slightly from the color values cited in the detailed botanical description, which accurately describe the color of 'RGLORS'.

DETAILED BOTANICAL DESCRIPTION

Figure 1:
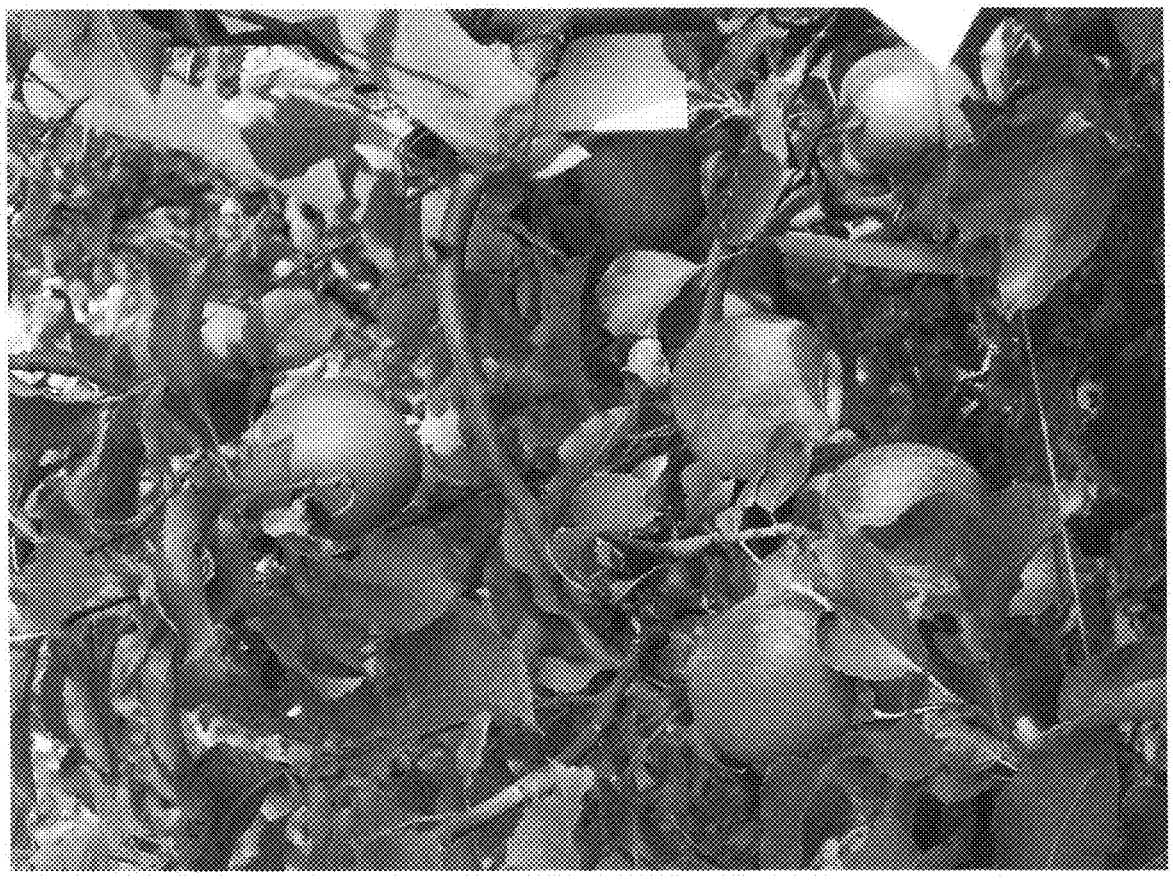
FIG. 1 shows the russet apples of 'RGLORS' originating on sport limb mutation of a 'Rosy Glow' tree, together with the bright red-pink solid blush apples on a non-mutated branch of the same 'Rosy Glow' tree.
Figure 2:
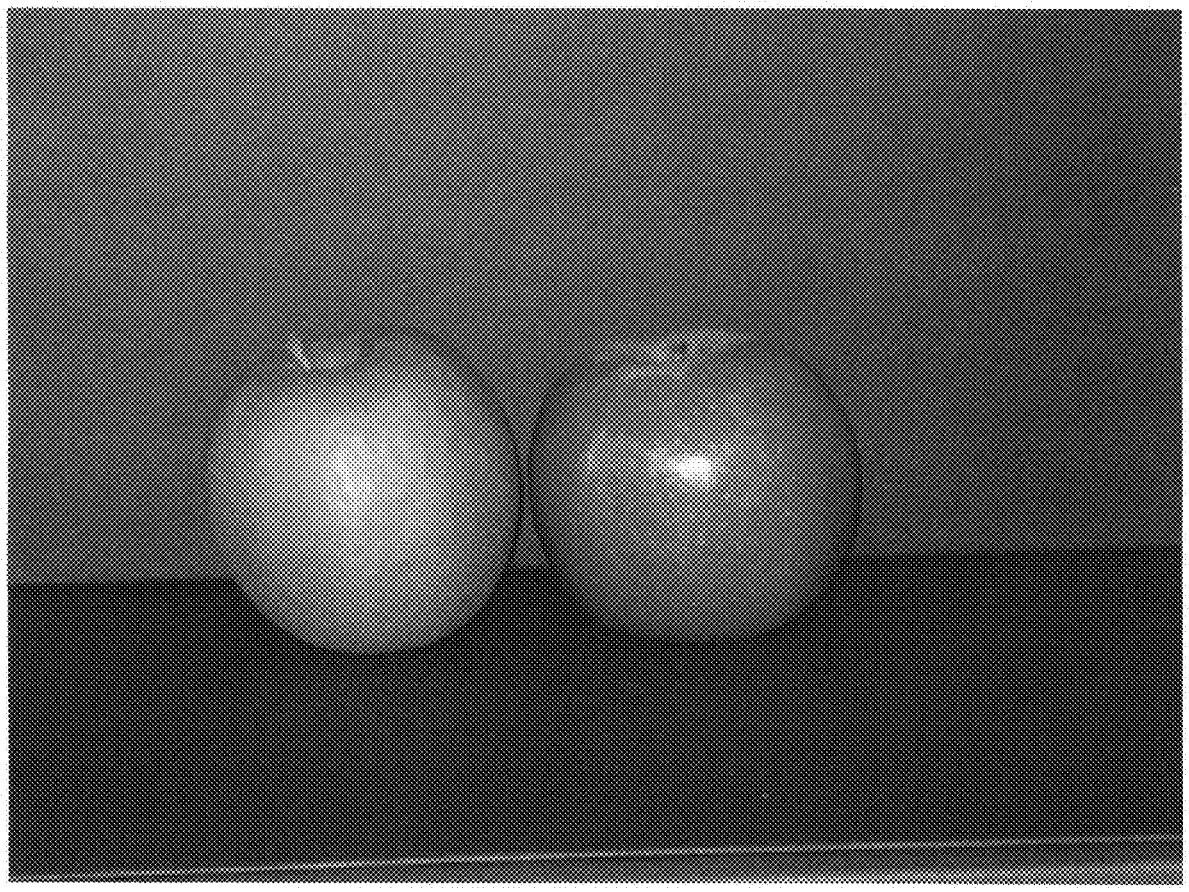
FIG. 2 shows a side view perspective of a russet apple of 'RGLORS' (on the left) compared to the bright red-pink solid blush apple of the non-mutated parent 'Rosy Glow' (on the right).
Figure 3:
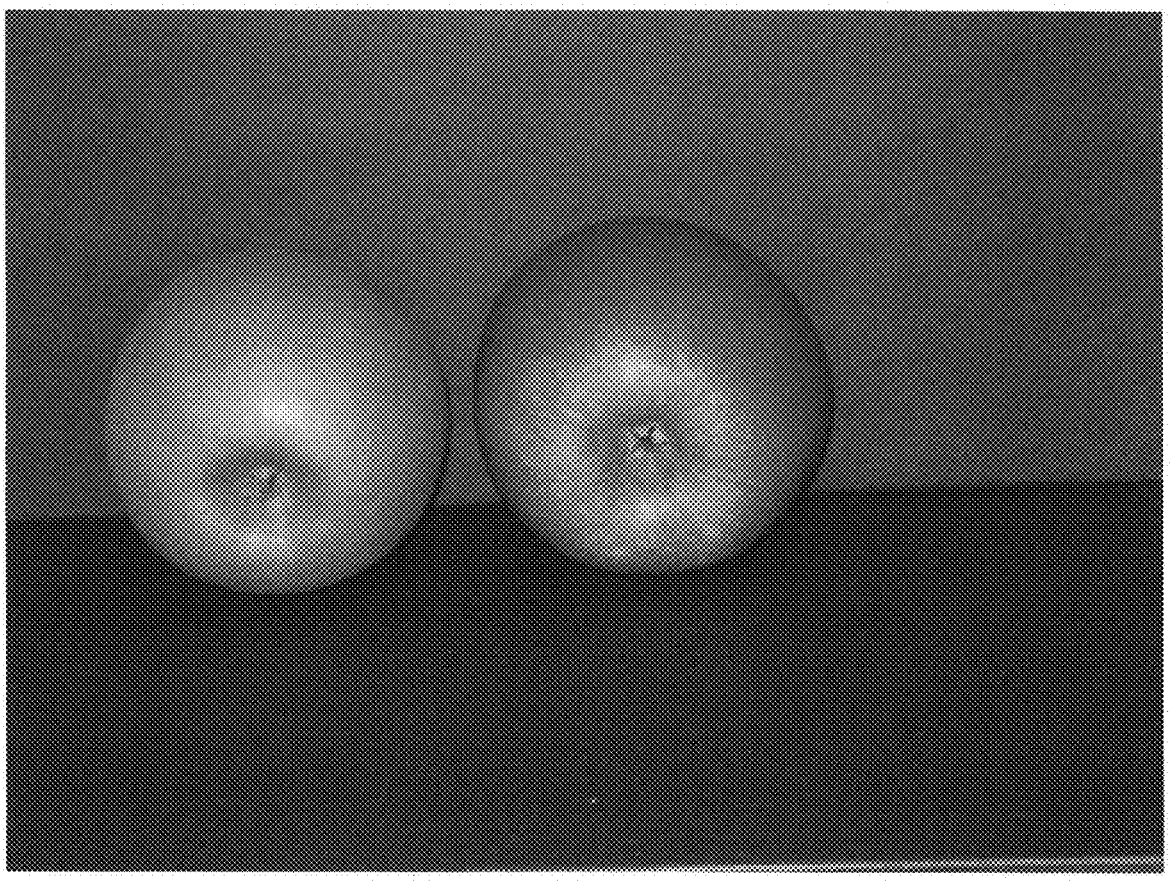
FIG. 3 shows a basal view perspective of a russet apple of 'RGLORS' (on the left) compared to the bright red-pink solid blush apple of the non-mutated parent 'Rosy Glow' (on the right).

The new *Malus* 'RGLORS' has not been observed under all possible environmental conditions. The phenotype of the new variety may vary with variations in environment such as temperature, light intensity, and day length without any change in the genotype of the apple tree.

The aforementioned photographs, together with the following observations, measurements and values describe trees of 'RGLORS' as grown in the apple farm in Migliaro, Ferrara, Italy, under conditions which closely approximate those generally used in commercial practice. The climate of the apple farm where 'RGLORS' is grown is temperate continental (about 44°48.36' North, 11°52.47' East) with high summer temperatures (maximum summer temperature of about 35° C.) and low winter temperatures (minimum winter temperature of about −5° C.). The soil of the apple farm where 'RGLORS' is grown is loamy-clay, and the trees are irrigated with a drip irrigation system. 'RGLORS' trees grafted on M9 rootstock (unpatented variety) are planted at a distance of about 3 feet by the trees and 12 feet by the rows, which is the typical orchard planting distance. The training system is by central leader.

Unless otherwise stated, the detailed botanical description includes observations, measurements and values based on three (3) year old 'RGLORS' trees that were grown in the apple farm in Migliaro, Ferrara, Italy, from 2007 to 2008. Quantified measurements are expressed as an average of measurements taken from a number of trees of 'RGLORS'. The measurements of any individual tree, or any group of trees, of the new variety may vary from the stated average.

Color references are made to The Royal Horticultural Society Colour Chart (R.H.S.), 2001 Edition, except where general colors of ordinary significance are used. Color values were taken under daylight conditions at approximately 3:00 p.m. in the apple farm in Migliaro, Ferrara, Italy.

All of the trees of 'RGLORS', insofar as they have been observed, have been identical in all the characteristics described below.

Classification:

*Botanical.*—*Malus domestica* Borkh.

Parentage: Limb sport mutation of *Malus domestica* Borkh. 'Rosy Glow' (unpatented, described in U.S. Publication No.: 2004/0168235).

Propagation:

*Type.*—Budding and grafting on M9 rootstock.

*Locality where grown and observed.*—Migliaro, Ferrara, Italy.

Growing conditions:

*Light intensities.*—Full sunlight or slight shade.

*Pruning or trimming requirements.*—Standard pruning and growing conditions.

Tree:

*Age.*—Observed trees were 3 years old.

*Vigor.*—Moderate vigor.

*Form.*—Upright, spreading and conical.

*Branching habit.*—Main branches angle about 60° to 90° with respect to trunk if allowed to grow naturally.

*Density.*—Medium density; about 3000 trees per hectare.

*Type of bearing.*—Early beginning of production; very high and constant productivity; regular and abundant flowering; no biennial bearing.

*Production* (*on* 3 *years old tree*).—About 12 kg per tree.

*Average size at maturity* (*on* 3 *years old tree*).—Height: About 2.5 m. Spread: About 0.9 m.

*Trunk caliper* (*at* 90 *cm above ground*).—About 3.5 cm to 4.5 cm.

*Trunk texture.*—Smooth with numerous lenticels.

*Trunk bark color.*—Primarily grey-brown. RHS 199A.

*Trunk lenticels.*—Length: About 3.0 mm. Width: About 2.0 mm. Color: Grey-brown, RHS 199C. Density: About 3 per $cm^2$.

*Branches.*—Number per tree: About 16. Angle: At emergence, angles range from 60° to 90°. Length (at 3 years): Varies due to conical shape of tree; maximum of 80 cm to 90 cm; minimum of 20 cm to 30 cm. Diameter (at 3 years): About 10 mm to 16 mm. Texture: Moderate pubescence on new wood, becoming glabrous on older wood. Color: Mature (after about 3 years): Grey-grown, RHS 199B. New Growth: Grey-purple, RHS 183A. Internode length: About 24 cm to 38 cm. Internode diameter: About 8 mm to 15 mm. Branch lenticels: Length: About 1 mm. Width: About 0.6 mm. Color: RHS 155B, white. Density: About 9 per $cm^2$.

*Spur.*—Present: Yes. Distance between each spur: On the 2 or 3 year old branches, the distance is about 25 mm to 38 mm. Number of fruit per spur: About 3 to 5.

Foliage:

*Arrangement.*—Alternate, simple, petiolated.

*Lamina.*—Average Size (from observation of 10 fully expanded leaves in October 2008 in Migliaro, Ferrara, Italy): Length: About 99 mm (range from 92 to 107 mm). Width: About 56 mm (range from 47 to 66 mm). Length/width ratio: 1.76. Overall Shape: Elliptical. Base shape: Obtuse. Apex shape: From acute to acuminate. Margin: Serrate. Texture: Upper surface: Glossy. Under surface: Slightly pubescent. Attitude in relation to shoot: Outwards. Color (mature leaves): Upper surface: RHS 137A, green. Under surface: RHS 146B, yellow-green. Venation: Type: Pinnate venation, from central vein to the leaf edge. Color: Greyed-green, RHS 195B.

*Petiole.*—Length: About 35 mm. Diameter: About 1.8 mm. Texture: Slightly pubescent. Color: Greyed-purple, RHS 185B.

*Stipule.*—Arrangement: Opposite. Length (distance of stipules from basal attachment of petiole): About 6 mm to 10 mm. Width: About 1.1 mm to 1.3 mm.

Inflorescence:

*Blooming time* (*Migliaro, Ferrara, Italy*).—First Bloom: On or about March 21$^{th}$. Full Bloom: On about March 30$^{th}$.

*Blooming period.*—About 15 to 18 days.

*Fragrance.*—Light, similar to other apple varieties.

*Number of flowers per inflorescence.*—About 4 to 6.

*Buds.*—Number per spur: About 1. Shape: Ellipsoid. Length: About 9.6 mm. Width: About 4.5 mm. Texture: Slightly pubescent. Color: Apex, greyed-purple, RHS 187A, and base, greyed-green, RHS 197C.

*Petals.*—Number per flower: Five. Size: Length: About 24 mm. Width: About 15 mm. Length/width ratio: 1.6. Overall shape: Ovate. Apex shape: Rounded. Base shape: Rounded. Texture (upper and under surfaces): Smooth. Margin: Free to touching. Color (when fully opened): Upper surface: White, RHS 155D, with traces of red-purple, RHS 65B. Under surface: White, RHS 155D, with traces of red-purple, RHS 68B. Color (unopened): Red purple, RHS 66A.

*Sepals.*—Number per flower: Five. Size: Length: About 8.1 mm. Width: About 3.8 mm. Overall shape: Pointed acute, recurved downward. Apex shape: Pointed acute. Texture (upper and under surfaces): Pubescent. Margin: Smooth. Color: Upper and under surfaces: Green, RHS 135B.

Fruit:

*Keeping quality.*—The fruit keeps very well on the tree. It can be stored in cold (+2° C.) temperature conditions for up to 6 months without loosing firmness and juiciness. It has a shelf life up to 2 weeks without loosing firmness and juiciness.

*Maturity when described.*—Early November.

*Maturity period after full bloom.*—About 220 days after full bloom on March 30th.

*Date of first and last picking* (*harvest*).—About November 2$^{nd}$ to November 15$^{th}$ in Migliaro, Ferrara, Italy.

*Type.*—Pome.

*General shape.*—Round, oblong, usually asymmetric, with non-prominent lobes at calyx ends.

*Average weight.*—About 248 g.

*Fruit size.*—Average height: About 78 mm. Average diameter (at widest point): About 75 mm. Position of maximum diameter: At about ½ of height near stem end.

*Stem.*—Length: About 20 to 25 mm. Diameter: About 2.5 mm. Color: Grey-brown, RHS 199B.

*Stem cavity.*—Depth: About 15 mm. Width: About 33 mm.

*Basin cavity.*—Depth: About 11 mm. Width: About 30 mm. Position of sepals: Erect or partly reflexed.

*Skin.*—Appearance: Thin; rough texture; absence of greasiness in storage. No evidence of cracking tendency observed with apple maturity. Thickness: Thin; about 0.4 mm. Texture: Rough. Bloom: Absent. Greasiness: Absent. Firmness (at picking time): 8.2 to 8.8 kg/cm$^2$. Color: Russet, closest to greyed-yellow, RHS 161A. Skin Lenticels: Length: About 0.8 mm. Width: About 0.8 mm. Color: Greyed-white, RHS 156D. Density: About 1.75 per cm$^2$.

*Flesh.*—Color: Yellow, RHS 11D. Texture: Crisp and juicy. Aroma: Mild. Flavor: Sour to sweet flavor, with sweet aftertaste. Eating quality: Good, with high level of sugar and acidity. Firmness (at picking time): About 18.2 pounds to 19.5 pounds. Soluble solids (at picking time): About 14.3% to 15.2%. Sugar content (at picking time): 15 to 16 Brix. Acidity/Starch (at picking time) 8.0 to 8.6 g/lt starch at 3 on a scale 1 to 5.

*Core.*—Symmetry of core: Symmetric with 10 bundles. Distinctness of core lines: Weak to medium. Length: About 32 mm. Width: About 30 mm.

*Locules.*—Number (per fruit): 5. Length: About 11 mm. Width: About 4.5 mm. Form: Partly open.

Seeds:

*Number per fruit.*—About 5 to 10.

*Number per locule.*—About 1 to 2.

*Shape.*—Obovate.

*Length.*—About 9 mm.

*Width.*—About 4.5 mm.

*Color.*—RHS 165A, grey-brown.

Use: Fresh market.

Disease/pest resistance: For both tree and fruit of 'RGLORS', similar to 'Rosy Glow', no unusual disease/pest resistance observed as of this time.

Disease/pest susceptibility: For both tree and fruit of 'RGLORS', similar to 'Rosy Glow', no unusual disease/pest susceptibility observed as of this time. Susceptible to *Venturia inaequalis.*

Winter hardiness: Tolerant to temperatures down to −10° C. without observed damage to wood and buds of dormant apple trees.

Drought/heat tolerance: Tolerant to temperatures up to 35° C., growth is limited by drought periods without irrigation.

Shipping/storage characteristics: Low sensitivity to bruising; good storability under ULO-conditions for up to 8 months.

We claim:

1. A new and distinct *Malus domestica* Borkh. apple tree variety named 'RGLORS', as illustrated and described herein.

* * * * *